United States Patent
Li et al.

(10) Patent No.: US 11,382,316 B2
(45) Date of Patent: Jul. 12, 2022

(54) TRANSGENIC MICE WITH INDUCIBLE NEURON-SPECIFIC INACTIVATION OF HUR GENE AND METHOD OF SCREENING

(71) Applicant: The Cleveland Clinic Foundation, Cleveland, OH (US)

(72) Inventors: Xiaoxia Li, Cleveland, OH (US); Tomasz Herjan, Beachwood, OH (US); Kevin Sun, Solon, OH (US); Xing Chen, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 162 days.

(21) Appl. No.: 16/446,274

(22) Filed: Jun. 19, 2019

(65) Prior Publication Data

US 2020/0015461 A1   Jan. 16, 2020

Related U.S. Application Data

(60) Provisional application No. 62/688,021, filed on Jun. 21, 2018.

(51) Int. Cl.
*A01K 67/027* (2006.01)
*G01N 33/00* (2006.01)
*C12N 15/85* (2006.01)

(52) U.S. Cl.
CPC ...... *A01K 67/0275* (2013.01); *A01K 67/0276* (2013.01); *C12N 15/8509* (2013.01); *A01K 2217/054* (2013.01); *A01K 2217/206* (2013.01); *A01K 2267/0312* (2013.01); *A01K 2267/0318* (2013.01); *C12N 2015/8527* (2013.01)

(58) Field of Classification Search
CPC ..................... A01K 67/0276; A01K 2217/206
USPC ................................................. 800/8, 18, 2
See application file for complete search history.

(56) References Cited

PUBLICATIONS

Katsanou (Mol. Cell. Biol., 2009, vol. 29, No. 10, p. 2762-2776.*
Elavl1tm1b(EUCOMM)Hmgu (Jaxson Lab 2012).*
MGI website Phenotype Term Detail for "impaired coordination", 2021.*
MGI website Phenotype Term Detail for "decreased grip strength", 2021.*
MGI website Phenotype Term Detail for "abnormal cerebral cortex morphology" 2021.*
MGI website Phenotype Term Detail for "motor neuron degeneration" 2021.*
Saberi, Neurol. Clin, 2015, vol. 33, p. 855-876.*
Thy1-Cre mouse (Jackson Lab, 2002).*
Dewachter (J. Neurosci., 2002, vol. 22, No. 9, p. 3445-3453).*
Garcia-Dominguez (Mol. Biol. of the Cell, 2011, vol. 22, p. 1227-1239).*
Chen (J Immunol., 2013, vol. 191, p. 5441-5450).*
Sun (J. Immunol., 2018, vol. 201, p. 157-166).*
Zhao (Development, 2020, vol. 147, p. 1-12).*
SJL-Tg(Thy1-CreERT2-EYFP)VGfng/J mouse described by Jackson Laboratory, 2008.*
Young (Nature Neurosci., 2008, vol. 11, No. 6, p. 721-728).*

* cited by examiner

*Primary Examiner* — Michael C Wilson
(74) *Attorney, Agent, or Firm* — Casimir Jones, S.C.; Jason R. Bond

(57) ABSTRACT

Provided herein non-human transgenic animals comprising a genome that: i) under-expresses, or is inducible to under-express, Hu Antigen R (HuR) in at least some neurons of said transgenic animal; ii) does not express HuR, or is inducible to not express HuR, in at least some neurons of said transgenic animal; or iii) does not express functional HuR, or is inducible to not express functional HuR in at least some neurons of said transgenic animal, as well as methods of screening drugs and therapies (e.g., useful in treating ALS) using such animals.

7 Claims, 6 Drawing Sheets
(4 of 6 Drawing Sheet(s) Filed in Color)

Specification includes a Sequence Listing.

SEQUENCE LISTING

<160> NUMBER OF SEQ ID NOS: 45

<210> SEQ ID NO 1
<211> LENGTH: 27
<212> TYPE: DNA
<213> ORGANISM: Artificial sequence
<220> FEATURE:
<223> OTHER INFORMATION: Synthetic primer/probe

<400> SEQUENCE: 1
ggtttccaaa tgtgtcagtt tcatagc                                   27

<210> SEQ ID NO 2
<211> LENGTH: 30
<212> TYPE: DNA
<213> ORGANISM: Artificial sequence
<220> FEATURE:
<223> OTHER INFORMATION: Synthetic primer/probe

<400> SEQUENCE: 2
agagatagat ggttaggcat agagatgcag                                30

<210> SEQ ID NO 3
<211> LENGTH: 26
<212> TYPE: DNA
<213> ORGANISM: Artificial sequence
<220> FEATURE:
<223> OTHER INFORMATION: Synthetic primer/probe

<400> SEQUENCE: 3
tatgctttaa gagacccaga agccag                                    26

<210> SEQ ID NO 4
<211> LENGTH: 21
<212> TYPE: DNA
<213> ORGANISM: Artificial sequence
<220> FEATURE:
<223> OTHER INFORMATION: Synthetic primer/probe

<400> SEQUENCE: 4
ttgccctctt attggtccag c                                         21

<210> SEQ ID NO 5
<211> LENGTH: 21
<212> TYPE: DNA
<213> ORGANISM: Artificial sequence
<220> FEATURE:
<223> OTHER INFORMATION: Synthetic primer/probe

<400> SEQUENCE: 5
ggggacctag agcaacttac t                                         21

<210> SEQ ID NO 6
<211> LENGTH: 23
<212> TYPE: DNA
<213> ORGANISM: Artificial sequence
<220> FEATURE:
<223> OTHER INFORMATION: Synthetic primer/probe

<400> SEQUENCE: 6
gcctatcgcc aagatttaga tga                                       23

<210> SEQ ID NO 7
<211> LENGTH: 21
<212> TYPE: DNA
<213> ORGANISM: Artificial sequence

```
<220> FEATURE:
<223> OTHER INFORMATION: Synthetic primer/probe

<400> SEQUENCE: 7
tgttcggggt taccttagtc a                                              21

<210> SEQ ID NO 8
<211> LENGTH: 19
<212> TYPE: DNA
<213> ORGANISM: Artificial sequence
<220> FEATURE:
<223> OTHER INFORMATION: Synthetic primer/probe

<400> SEQUENCE: 8
tgggcttcgt tgcctatgc                                                 19

<210> SEQ ID NO 9
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 9
gctggtcggg agtcagaaag                                                20

<210> SEQ ID NO 10
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 10
ctcatccgcg tttactccat                                                20

<210> SEQ ID NO 11
<211> LENGTH: 19
<212> TYPE: DNA
<213> ORGANISM: Artificial sequence
<220> FEATURE:
<223> OTHER INFORMATION: Synthetic primer/probe

<400> SEQUENCE: 11
gctcctctta ggggccact                                                 19

<210> SEQ ID NO 12
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 12
agcaggtcat caagtcaggc                                                20

<210> SEQ ID NO 13
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 13
tctcacaaac ccctcgacat                                                20
```

```
<210> SEQ ID NO 14
<211> LENGTH: 23
<212> TYPE: DNA
<213> ORGANISM: Artificial sequence
<220> FEATURE:
<223> OTHER INFORMATION: Synthetic primer/probe

<400> SEQUENCE: 14
ttgataagca tgagggaaga cca                                              23

<210> SEQ ID NO 15
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 15
ggagcaggac agttggagtg                                                  20

<210> SEQ ID NO 16
<211> LENGTH: 21
<212> TYPE: DNA
<213> ORGANISM: Artificial sequence
<220> FEATURE:
<223> OTHER INFORMATION: Synthetic primer/probe

<400> SEQUENCE: 16
cctttgccat gtgttctgtc t                                                21

<210> SEQ ID NO 17
<211> LENGTH: 21
<212> TYPE: DNA
<213> ORGANISM: Artificial sequence
<220> FEATURE:
<223> OTHER INFORMATION: Synthetic primer/probe

<400> SEQUENCE: 17
cgacaaccac aacggtgata g                                                21

<210> SEQ ID NO 18
<211> LENGTH: 21
<212> TYPE: DNA
<213> ORGANISM: Artificial sequence
<220> FEATURE:
<223> OTHER INFORMATION: Synthetic primer/probe

<400> SEQUENCE: 18
gccgaagttg cagtggaagt a                                                21

<210> SEQ ID NO 19
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 19 tccccctggaa aacaacagag                                                 20

<210> SEQ ID NO 20
<211> LENGTH: 23
<212> TYPE: DNA
<213> ORGANISM: Artificial sequence
<220> FEATURE:
<223> OTHER INFORMATION: Synthetic primer/probe
```

```
<400> SEQUENCE: 20
tcaaacgact atacccaaca agc                                           23

<210> SEQ ID NO 21
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 21
atgacatcaa gaaggtggtg                                               20

<210> SEQ ID NO 22
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 22
ggtcatcact attggcaacg                                               20

<210> SEQ ID NO 23
<211> LENGTH: 21
<212> TYPE: DNA
<213> ORGANISM: Artificial sequence
<220> FEATURE:
<223> OTHER INFORMATION: Synthetic primer/probe

<400> SEQUENCE: 23
aaccagttgt gttgtcagga c                                             21

<210> SEQ ID NO 24
<211> LENGTH: 19
<212> TYPE: DNA
<213> ORGANISM: Artificial sequence
<220> FEATURE:
<223> OTHER INFORMATION: Synthetic primer/probe

<400> SEQUENCE: 24
gattgtggcc ttctttgag                                                19

<210> SEQ ID NO 25
<211> LENGTH: 21
<212> TYPE: DNA
<213> ORGANISM: Artificial sequence
<220> FEATURE:
<223> OTHER INFORMATION: Synthetic primer/probe

<400> SEQUENCE: 25
tagcgactgt tctgttccca c                                             21

<210> SEQ ID NO 26
<211> LENGTH: 23
<212> TYPE: DNA
<213> ORGANISM: Artificial sequence
<220> FEATURE:
<223> OTHER INFORMATION: Synthetic primer/probe

<400> SEQUENCE: 26
aaattgggat tagcacctct gag                                           23

<210> SEQ ID NO 27
```

```
<211> LENGTH: 21
<212> TYPE: DNA
<213> ORGANISM: Artificial sequence
<220> FEATURE:
<223> OTHER INFORMATION: Synthetic primer/probe

<400> SEQUENCE: 27
ttctggattt aaccggacag c                                          21

<210> SEQ ID NO 28
<211> LENGTH: 19
<212> TYPE: DNA
<213> ORGANISM: Artificial sequence
<220> FEATURE:
<223> OTHER INFORMATION: Synthetic primer/probe

<400> SEQUENCE: 28
acccgtctct acaggccac                                             19

<210> SEQ ID NO 29
<211> LENGTH: 21
<212> TYPE: DNA
<213> ORGANISM: Artificial sequence
<220> FEATURE:
<223> OTHER INFORMATION: Synthetic primer/probe

<400> SEQUENCE: 29
agaatggggt gttctttgtg c                                          21

<210> SEQ ID NO 30
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 30
ggtgactttc cgggtcttgg                                            20

<210> SEQ ID NO 31
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 31
tgttctgttc gatgctcagg                                            20

<210> SEQ ID NO 32
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 32
attggggacc cttaggccat                                            20

<210> SEQ ID NO 33
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 33
```

```
gatgtagctg gtgttgggct                                                  20

<210> SEQ ID NO 34
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 34
agcatcctgg aacacctgaa                                                  20

<210> SEQ ID NO 35
<211> LENGTH: 23
<212> TYPE: DNA
<213> ORGANISM: Artificial sequence
<220> FEATURE:
<223> OTHER INFORMATION: Synthetic primer/probe

<400> SEQUENCE: 35
ggcagtcccc tgatttacat aga                                              23

<210> SEQ ID NO 36
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 36
gacgaatggc tgagtacaga                                                  20

<210> SEQ ID NO 37
<211> LENGTH: 22
<212> TYPE: DNA
<213> ORGANISM: Artificial sequence
<220> FEATURE:
<223> OTHER INFORMATION: Synthetic primer/probe

<400> SEQUENCE: 37
ccacggccta gtttctcaga ta                                               22

<210> SEQ ID NO 38
<211> LENGTH: 23
<212> TYPE: DNA
<213> ORGANISM: Artificial sequence
<220> FEATURE:
<223> OTHER INFORMATION: Synthetic primer/probe

<400> SEQUENCE: 38
accatgtgat aatcagagcg atg                                              23

<210> SEQ ID NO 39
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 39
taccgtcgct caaatcgctg                                                  20

<210> SEQ ID NO 40
<211> LENGTH: 20
<212> TYPE: DNA
```

<213> ORGANISM: Artificial sequence
<220> FEATURE:
<223> OTHER INFORMATION: Synthetic primer/probe

<400> SEQUENCE: 40
ccagacgagc ctttgagaag                                                    20

<210> SEQ ID NO 41
<211> LENGTH: 21
<212> TYPE: DNA
<213> ORGANISM: Artificial sequence
<220> FEATURE:
<223> OTHER INFORMATION: Synthetic primer/probe

<400> SEQUENCE: 41
tggccgtatc ctgaagtgtc a                                                  21

<210> SEQ ID NO 42
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 42
cataccagga aatgagcttg                                                    20

<210> SEQ ID NO 43
<211> LENGTH: 20
<212> TYPE: DNA
<213> ORGANISM: Artificial sequence
<220> FEATURE:
<223> OTHER INFORMATION: Synthetic primer/probe

<400> SEQUENCE: 43
acggatgtca acgtcacact                                                    20

<210> SEQ ID NO 44
<211> LENGTH: 23
<212> TYPE: DNA
<213> ORGANISM: Artificial sequence
<220> FEATURE:
<223> OTHER INFORMATION: Synthetic primer/probe

<400> SEQUENCE: 44
ccaccatgtt tcttagagtg agg                                                23

<210> SEQ ID NO 45
<211> LENGTH: 19
<212> TYPE: DNA
<213> ORGANISM: Artificial sequence
<220> FEATURE:
<223> OTHER INFORMATION: Synthetic primer/probe

<400> SEQUENCE: 45
caaactgagc agagtcttc                                                     19

TRANSGENIC MICE WITH INDUCIBLE NEURON-SPECIFIC INACTIVATION OF HUR GENE AND METHOD OF SCREENING

The present application claim priority to U.S. provisional application Ser. No. 62/688,021 filed Jun. 21, 2018, which is herein incorporated by reference in its entirety.

This invention was made with government support under NS069765 awarded by the National Institutes of Health (NIH). The government has certain rights in the invention.

FIELD

Provided herein non-human transgenic animals comprising a genome that: i) under-expresses, or is inducible to under-express, Hu Antigen R (HuR) in at least some neurons of said transgenic animal; ii) does not express HuR, or is inducible to not express HuR, in at least some neurons of said transgenic animal; or iii) does not express functional HuR, or is inducible to not express functional HuR in at least some neurons of said transgenic animal, as well as methods of screening drugs and therapies (e.g., useful in treating ALS) using such animals.

BACKGROUND

Amyotrophic Lateral Sclerosis (ALS) is a neurodegenerative disease that is characterized by neuronal cell death. Symptoms include stiff muscles, twitching, atrophy, and eventual paralysis (1, 2). A vast majority of ALS cases (90%-95%) have an unknown cause; 5%-10% of cases are inherited (2). Currently, there is no cure for ALS, although treatments are available to improve prognosis and quality of life (3). The genetic linkage of the RNA-binding proteins TAR DNA binding protein 43 (TDP-43) and fused in sarcoma/translocated in liposarcoma (FUS/TLS) to ALS implicates RNA regulation as a critical mechanism of motor neuron degeneration in ALS. Recent studies have found that TDP-43 and FUS may play a crucial molecular role in ALS by translocating from the nucleus to the cytoplasm and aggregating into stress granules in neurons (4).

SUMMARY

Provided herein non-human transgenic animals comprising a genome that: i) under-expresses (e.g., compared to wild-type levels of expression), or is inducible to under-express, Hu Antigen R (HuR) in at least some neurons (e.g., 10% . . . 25% . . . 50% . . . 75% . . . or more) of said transgenic animal; ii) does not express HuR (e.g., no detectable expression), or is inducible to not express HuR, in at least some neurons of said transgenic animal; or iii) does not express functional HuR, or is inducible to not express functional HuR in at least some neurons of said transgenic animal, as well as methods of screening drugs and therapies (e.g., useful in treating ALS) using such animals.

In some embodiments, provided herein are non-human transgenic animal comprising a genome that: i) under-expresses, or is inducible to under-express, Hu Antigen R (HuR) in at least some neurons of the transgenic animal; ii) does not express HuR, or is inducible to not express HuR, in at least some neurons of the transgenic animal; or iii) does not express functional HuR, or is inducible to not express functional HuR in at least some neurons of the transgenic animal.

In particular embodiments, the non-human transgenic animals herein have a genome that comprises a heterologous genetic construct. In other embodiments, the genetic construct comprises a neuron-specific promoter (e.g., any one of the neuron-specific promoters that are known in the art). In further embodiments, the genetic construct further comprises at least one recombinase sequence inducible by an exogenous agent, wherein the recombinase sequence, once induced, mediates the deletion of the HuR gene in the transgenic animal.

In certain embodiments, the animal is selected from the group consisting of a mouse, a rat, a dog, and a rabbit. In further embodiments, the at least some neuron cells are in the transgenic animals brain or spinal cord. In other embodiments, the animal displays symptoms of, or similar to, amyotrophic lateral sclerosis (ALS).

In some embodiments, provided herein are methods of screening an intervention for a disease or condition, comprising: a) contacting any of the transgenic animals described herein with a candidate intervention; and b) determining the effect of the intervention on a disease or condition in the transgenic animal. In further embodiments, the intervention is selected from the group consisting of a drug, a lifestyle change, an alternative medicine therapy, and a combination thereof. In particular embodiments, the disease is ALS.

In some embodiments, provided herein is the use of any of the transgenic animals described herein to screen for an intervention for a disease or condition.

DESCRIPTION OF THE FIGURES

The patent or application file contains at least one drawing executed in color. Copies of this patent or patent application publication with color drawings will be provided by the Office upon request and payment of the necessary fee.

DETAILED DESCRIPTION

Figure 1:
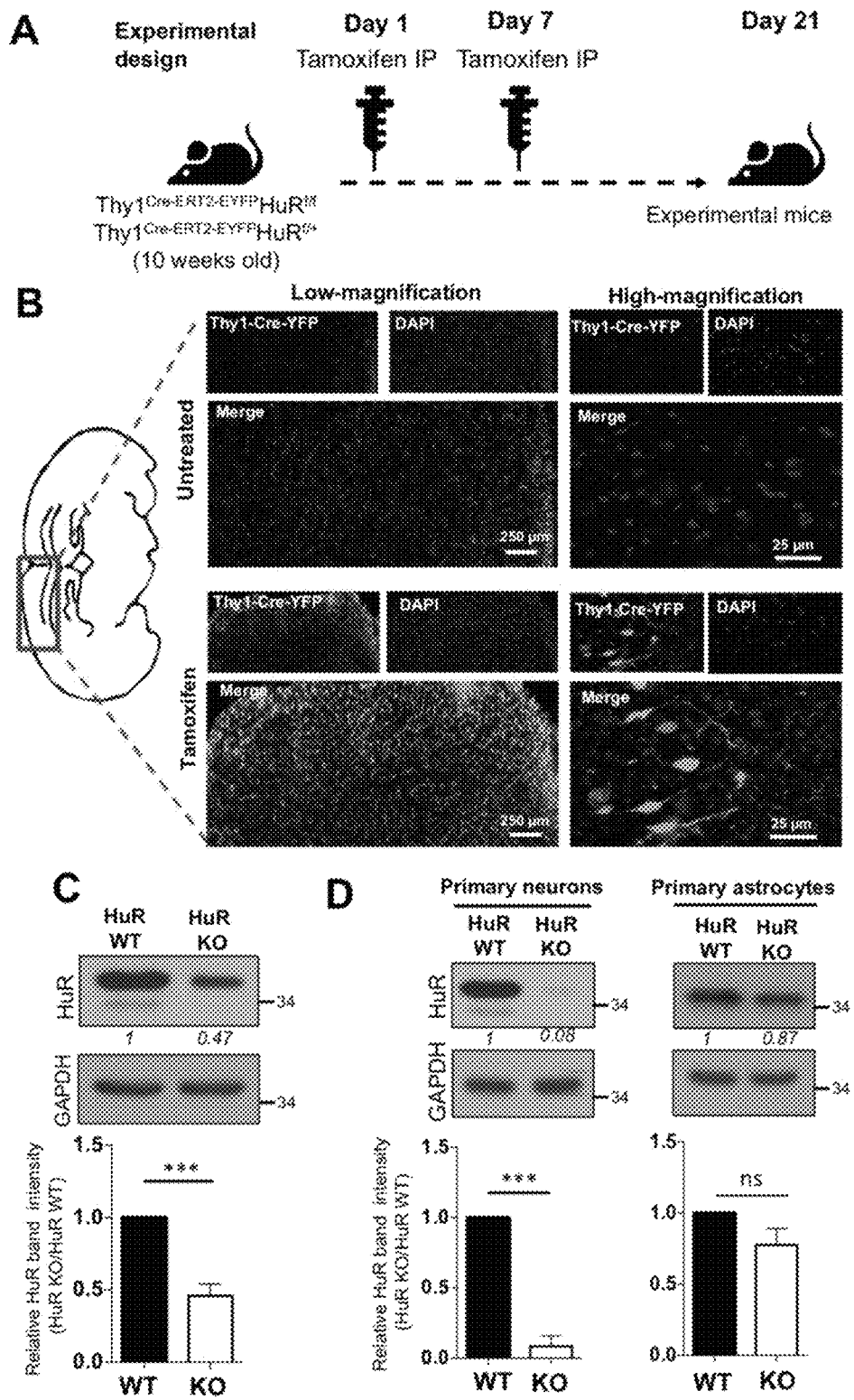
FIG. 1, panels A-D. Generation of neuron-specific HuR-deficient mice. Panel A. Tamoxifen was administered to conditional neuron-specific HuR-deficient (Thy1$^{Cre-ERT2-EYFP}$HuR$^{f/f}$) and age-matched control (Thy1$^{Cre-ERT2-EYFP}$HuR$^{f/+}$) mice at 10 and 11 weeks of age. Three weeks (21 days) after first tamoxifen injection, these mice (referred to as experimental mice) were subjected to the experiments in FIG. 1, panels B-C and FIG. 2, panels A-D. Panel B. The representative confocal images of Cre-YFP in brain sections of neuron-specific HuR-deficient (Thy1$^{Cre-ERT2-EYFP}$HuR$^{f/f}$) mice either untreated or treated with tamoxifen as in A, Nuclei were stained with DAPI (blue). Panel C. Western blot analysis of HuR in lysates from brain tissue of neuron-specific HuR-deficient (Thy1$^{Cre-ERT2-EYFP}$HuR$^{f/f}$) and control (Thy1$^{Cre-ERT2-EYFP}$HuR$^{f/+}$) mice after tamoxifen injection. Western blots were quantified by densitometry using ImageJ, error bars represent s.d. of biological replicates (N=15 mice for both KO and WT), *p<0.05 by two-tailed Student's t test. Panel D. Western blot analysis of HuR in lysates from tamoxifen treated primary neurons and astrocytes isolated from HuR-deficient (Thy1$^{Cre-ERT2-EYFP}$HuR$^{f/f}$) and control (Thy1$^{Cre-ERT2-EYFP}$HuR$^{f/+}$) mice. Western blots were quantified by densitometry using ImageJ, error bars represent s.d. of biological replicates (N=15 mice for both KO and WT), *p<0.001 by two-tailed Student's t test.

Provided herein non-human transgenic animals comprising a genome that: i) under-expresses, or is inducible to under-express, Hu Antigen R (HuR) in at least some neurons of said transgenic animal; ii) does not express HuR, or is inducible to not express HuR, in at least some neurons of said transgenic animal; or iii) does not express functional HuR, or is inducible to not express functional HuR in at least some neurons of said transgenic animal, as well as methods of screening drugs and therapies (e.g., useful in treating ALS) using such animals.

ELAV-like protein 1, or Human antigen R (HuR), is an RNA binding protein in the ELAVL protein family that selectively binds to AU-rich elements (AREs) found in 3' untranslated regions of mRNA (5). Unlike other members of the ELAVL protein family, HuR is ubiquitously expressed in both neuronal and non-neuronal cells. Importantly, there is no available HuR-related genetic animal model that specifically targets neuronal cells with a phenotype that can simulate ALS and its related signature markers. In order to investigate the potential role of HuR specifically in neurons, we developed inducible neuron-specific HuR-deficient mice using neuron-specific Thy1 promoter to robustly drive both Cre recombinase and yellow fluorescent protein (YFP) expression. The Cre recombinase under the control of estrogen receptor is activated by tamoxifen, which translocates to the nucleus and mediates the deletion of the floxed HuR gene.

After tamoxifen-induced deletion of HuR, these mice developed a phenotype composed of poor balance, decreased movement, and decreased strength, which were quantified by an array of behavioral tests (including an open-field test, a Y-maze test, a rotarod test, and a grip strength test). These results demonstrate a motor deficiency phenotype in neuron-specific HuR-deficient mice. In support of this, immunostaining of brain and spinal cord sections indicated neuronal cell death in pyramidal neurons and alpha motor neurons of HuR-deficient mice. Moreover, microarray and RT-PCR analyses identified genes with altered expression in brain tissue of neuron-specific HuR-deficient mice, including genes important for cell growth and immune regulation. Some of the HuR-regulated genes are also significantly altered in the brain and spinal cord of ALS patients. These findings suggest that the molecular signature and neuropathology shown by the neuron-specific HuR-deficient mice can be explored as a model system to study ALS.

The HuR-deficient, or inducible HuR-deficient, transgenic animals disclosed herein find use, for example, in drug (e.g., ALS) screens. In some embodiments, test compounds (e.g., a drug that is suspected of being useful to treat ALS, or a compound from a compound library) and control compounds (e.g., a placebo) are administered to the transgenic animals and the control animals and the effects evaluated.

The HuR-deficient, or inducible HuR-deficient, transgenic animals can be generated via a variety of methods (see, e.g., Example 1). In some embodiments, embryonal cells at various developmental stages are used to introduce transgenes for the production of HuR-deficient, or inducible HuR-deficient, transgenic animals. Different methods are used depending on the stage of development of the embryonal cell. The zygote is a good target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (e.g., Brinster et al., Proc. Natl. Acad. Sci. USA 82:4438-4442 (1985), herein incorporated by reference). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety. Additional methods for generating transgenic animal are described, for example, in Palmiter, Ann. Rev. Genet. 20:465-99 (1986); Gordon, Methods in enzymology, vol. 225; and Camper, Biotechniques. Vol 5. No 7. (1987); each of which is herein incorporated by reference in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (see, e.g., U.S. Pat. No. 6,080,912, incorporated herein by reference). In other embodiments, the developing non-human embryo can be cultured in vitro to the blastocyst stage. During this time, the blastomeres can be targets for retroviral infection (e.g., Janenich, Proc. Natl. Acad. Sci. USA 73:1260 (1976), herein incorporated by reference). Efficient infection of the blastomeres is obtained by enzymatic treatment to remove the zona pellucida (e.g., Hogan et al., in *Manipulating the Mouse Embryo*, Cold Spring Harbor Laboratory Press, Cold Spring Harbor, N.Y. (1986), herein incorporated by reference). The viral vector system used to introduce the transgene is typically a replication-defective retrovirus carrying the transgene (e.g., Jahner et al., Proc. Natl. Acad Sci. USA 82:6927 (1985), herein incorporated by reference). Transfection is easily and efficiently obtained by culturing the blastomeres on a monolayer of virus-producing cells (e.g., Stewart, et al., EMBO J., 6:383 (1987), herein incorporated by reference). Alternatively, infection can be performed at a later stage. Virus or virus-producing cells can be injected into the blastocele (e.g., Jahner et al., Nature 298:623 (1982), herein incorporated by reference). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (e.g., Jahner et al., supra (1982)). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 (1990), and Haskell and Bowen, Mol. Reprod. Dev., 40:386 (1995); both of which are herein incorporated by reference).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 (1981); Bradley et al., Nature 309:255 (1984); Gossler et al., Proc. Acad. Sci. USA 83:9065 (1986); and Robertson et al., Nature 322:445 (1986); all of which are herein incorporated by refernece). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 (1988), herein incorporated by reference). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel. In still other embodiments, homologous recombination is utilized to knock-out gene function or create deletion mutants (e.g., truncation mutants). Methods for homologous recombination are described in U.S. Pat. No. 5,614,396, incorporated herein by reference.

In some embodiments, the present disclosure provides drug screening assays (e.g., to screen for drugs to treat autoimmune disease). Specifically, the present disclosure provides screening methods for identifying modulators, i.e., candidate or test compounds or agents (e.g., proteins, peptides, peptidomimetics, peptoids, small molecules or other drugs) which decrease symptoms of ALS disease. In certain embodiments, a small molecule library is screened for such activity in the animal models herein.

In certain embodiments, drug screening methods of the present disclosure utilize HuR-deficient, or inducible HuR-deficient, transgenic animals. In some embodiments, the transgenic animals exhibit symptoms characteristic of ALS. For example, in some embodiments, test compounds are administered to transgenic animals of the present disclosure and the effect of the test compound on transgene expression and/or function is assayed. In other embodiments, test compounds are administered to transgenic animals of the present disclosure and the effect of the test compound on ALS type symptoms in the animal is assessed.

The test compounds of the present disclosure can be obtained using any suitable method, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 (1994), herein incorporated by reference); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145, herein incorporated by reference).

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994).

Libraries of compounds may be presented in solution (e.g., Houghten, Biotechniques 13:412-421 (1992)), or on beads (Lam, Nature 354:82-84 (1991)), chips (Fodor, Nature 364:555-556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386-390 (1990); Devlin Science 249:404-406 (1990); Cwirla et al., Proc. Nati. Acad. Sci. 87:6378-6382 (1990); Felici, J. Mol. Biol. 222: 301 (1991)).

In some embodiments, test compound are candidate ALS therapies or interventions (e.g., including but not limited to, non-steroidal anti-inflammatory agents, anti-malarial drug, corticosteroids (system and topical), immunosuppressants, biologics, alternative medicine (e.g., DHEA, fish oil, acupuncture), dietary changes, lifestyle changes, and combinations thereof). Embodiments of this disclosure further pertain to novel agents identified by the above-described screening methods.

EXAMPLES

Example 1

Neuron-Specific HuR-Deficient Mice

Human antigen R (HuR), is an RNA binding protein in the human antigen protein family. To study the neuron-specific function of HuR, we generated inducible, neuron-specific HuR-deficient mice of both sexes. After tamoxifen-induced deletion of HuR, these mice developed a phenotype consisting of poor balance, decreased movement, and decreased strength. They performed significantly worse on the rotarod test compared to littermate control mice, indicating coordination deficiency. Using the grip strength test, it was also determined that the forelimbs of neuron-specific HuR-deficient mice were much weaker than littermate control mice.

Immunostaining of the brain and cervical spinal cord showed that HuR-deficient neurons had increased levels of cleaved Caspase 3, a hallmark of cell apoptosis. Caspase 3 cleavage was especially strong in pyramidal neurons and alpha motor neurons of HuR-deficient mice. Genome-wide microarray and RT-PCR analysis further indicated that HuR deficiency in neurons resulted in altered expression of genes in the brain involved in cell growth, including Tchp, Cdkn2c, GPSM2, Ier2, SOD1, and Bcl2. The additional enriched GO terms in the brain tissues of neuron-specific HuR-deficient mice were largely related to inflammation, including interferon-induced genes and complement components. Importantly, some of these HuR-regulated genes were also significantly altered in the brain and spinal cord of patients with amyotrophic lateral sclerosis. Additionally, neuronal HuR deficiency resulted in the redistribution of TDP43 to cytosolic granules, which has been linked to motor neuron disease.

Materials and Methods:
Reagents:
Antibodies against GAPDH, HuR, anti-Nur-77 (sc-166166) were purchased from Santa Cruz Biotechnology. Anti-TDP-43 and anti-ChaT was from Proteintech, anti-NeuN (MAB377) was from Milipore, anti-cleaved Caspase 3 was from Cell Signaling, anti-CD3 was from Abcam, anti-Ier2 (orb157617) was obtained from Biorbyt. B6; SJL-Tg(Thy1-cre/ERT2,-EYFP)VGfng/J mice were obtained from The Jackson Laboratory. These mice were crossed to HuR flox/flox mice (described previously (7)) to generate conditional neuron-specific HuR KO mice (Thy1$^{Cre\text{-}ERT2\text{-}EYFP}$HuR$^{f/f}$) and control mice (Thy1$^{Cre\text{-}ERT2\text{-}EYFP}$HuR$^{f/f}$). Cre expression was induced via intraperitoneal injection of Tamoxifen (SIGMA) (~5 mg/25 g weight, twice). Mice of both sexes were used for experiments. The Cleveland Clinic Institutional Animal Care and Use Committee reviewed and approved all animal experiments.

Primary Cell Culture:

Primary astrocyte culture was prepared from 1- to 2-day-old mice. Briefly, Brains freed of meninges were dissociated with 1 ml pipettes. Debris was removed by filtration with a 40 μm cell strainer (Falcon). The attached cells were cultured in DMEM plus 10% FBS supplemented with 50 μg/ml penicillin and 50 μg/ml streptomycin. Astrocytes were confirmed by staining with anti-glial fibrillary acidic protein (GFAP) (Santa cruz) and purity was >90%. Neurons were prepared from the pups at E15. Brains were dissociated with 1ml pipettes and the debris removed using a 70 μm cell strainer (Falcon). Cells were cultured in Neuronbasal media (Invitrogen) plus B-27 (invitrogen) and 50 μg/ml penicillin and 50 μg/ml streptomycin. >90% of these cultured cells were positive for MAP2 (a marker for neurons, anti-MAP2 from Abcam). Cre expression was induced with tamoxifen at 0.02 mg/ml for 3 consecutive days.

Collection of Tissue and Immunofluorescence:

Briefly, mice were perfused with 4% paraformaldehyde/phosphate-buffered saline (PBS), brains/spinal cords were collected and post-fixed for 24 h in 4% paraformaldehyde/PBS at 4° C., and snap-frozen in OCT medium followed by cryosectioning at 10 μm. For immunofluorescent staining, frozen tissue sections was fixed and permeabilized with 4% paraformaldehyde solution containing 0.2% Triton X-1100 for 10 minutes. 10% normal goat serum was used as a blocking agent. Sections were incubated in PBS/0.2% Triton X-100/10% goat serum with appropriate primary and secondary antibodies and used for immunofluorescent staining followed by microscopic analysis.

RNA-Binding Assays RIP:

10×10$^6$ NSC-34 cells were trypsinized, washed twice, and re-suspended in 10 ml ice-cold PBS. Cells were fixed in 0.1% formaldehyde for 15 min at room temperature, whereupon the cross-linking reaction was stopped with glycine (pH 7; 0.25 M). The cells were then washed twice with ice-cold PBS, re-suspended in 2 ml RIPA buffer (50 mM Tris-HCl [pH 7.5], 1% Nonidet P-40, 0.5% sodium deoxycholate, 0.05% SDS, 1 mM EDTA, 150 mM NaCl, and proteinase inhibitors), and sonicated. The lysate was centrifuged (15 min, 4° C., 16,000×g), and 1 ml each supernatant was immunoprecipitated overnight at 4° C., using Dynabeads (invitrogen) pre-incubated with 20 μg anti-HuR or anti-IgG Ab. The beads were washed five times with 1 ml RIPA buffer and re-suspended in 150 μl elution buffer (50 mM Tris-Cl [pH 7], 5 mM EDTA, 10 mM DTT, 1% SDS). Cross-linking was reversed by incubation at 70° C. for 45 min, RNA was purified from immunoprecipitates with Trizol (Invitrogen) according to the manufacturer's instructions and treated with RNase-free DNase, and cDNAs were synthesized and 10% (two microliters) of the reverse transcriptase product was subjected to quantitative real-time PCR. Primers used for quantitative real-time PCR are listed in Table 1.

TABLE 1

Real-time PCR primers

| Gene | SEQ ID NO.: | Forward primer | SEQ ID NO.: | Reverse primer |
| --- | --- | --- | --- | --- |
| Tchp | 4 | TTGCCCTCTTATTGGTCCAGC | 25 | TAGCGACTGTTCTGTTCCCAC |
| Cdkn2c | 5 | GGGGACCTAGAGCAACTTACT | 26 | AAATTGGGATTAGCACCTCTGAG |
| Ifit1 | 6 | GCCTATCGCCAAGATTTAGATGA | 27 | TTCTGGATTTAACCGGACAGC |
| Bst2 | 7 | TGTTCGGGGTTACCTTAGTCA | 28 | ACCCGTCTCTACAGGCCAC |
| Ifitm2 | 8 | TGGGCTTCGTTGCCTATGC | 29 | AGAATGGGGTGTTCTTTGTGC |
| Hmga1 | 9 | GCTGGTCGGGAGTCAGAAAG | 30 | GGTGACTTTCCGGGTCTTGG |
| C2 | 10 | CTCATCCGCGTTTACTCCAT | 31 | TGTTCTGTTCGATGCTCAGG |
| Col1a1 | 11 | GCTCCTCTTAGGGGCCACT | 32 | ATTGGGGACCCTTAGGCCAT |
| C3 F | 12 | AGCAGGTCATCAAGTCAGGC | 33 | GATGTAGCTGGTGTTGGGCT |
| C4b F | 13 | TCTCACAAACCCCTCGACAT | 34 | AGCATCCTGGAACACCTGAA |
| Gpsm2 F | 14 | TTGATAAGCATGAGGGAAGACCA | 35 | GGCAGTCCCCTGATTTACATAGA |
| Chaf1a F | 15 | GGAGCAGGACAGTTGGAGTG | 36 | GACGAATGGCTGAGTACAGA |
| Arfip1 F | 16 | CCTTTGCCATGTGTTCTGTCT | 37 | CCACGGCCTAGTTTCTCAGATA |
| Trdn F | 17 | CGACAACCACAACGGTGATAG | 38 | ACCATGTGATAATCAGAGCGATG |
| Ier2 F | 18 | GCCGAAGTTGCAGTGGAAGTA | 39 | TACCGTCGCTCAAATCGCTG |
| TDP43 F | 19 | TCCCCTGGAAAACAACAGAG | 40 | CCAGACGAGCCTTTGAGAAG |
| FUS F | 20 | TCAAACGACTATACCCAACAAGC | 41 | TGGCCGTATCCTGAAGTGTCA |
| GAPDH F | 21 | ATGACATCAAGAAGGTGGTG | 42 | CATACCAGGAAATGAGCTTG |

TABLE 1-continued

Real-time PCR primers

| Gene | SEQ ID NO.: | Forward primer | SEQ ID NO.: | Reverse primer |
|---|---|---|---|---|
| b-actin F | 22 | GGTCATCACTATTGGCAACG | 43 | ACGGATGTCAACGTCACACT |
| SOD1 | 23 | AACCAGTTGTGTTGTCAGGAC | 44 | CCACCATGTTTCTTAGAGTGAGG |
| Bcl2 | 24 | GATTGTGGCCTTCTTTGAG | 45 | CAAACTGAGCAGAGTCTTC |

RIP data analysis: Ct value of each RIP RNA fractions was normalized to the Input RNA fraction Ct value for the same qPCR Assay (ΔCt) to account for RNA sample preparation differences. Then the normalized RIP fraction Ct value (ΔCt) was adjusted for the normalized background (anti-IgG) [non-specific (NS) Ab] fraction Ct value (ΔΔCt). The fold enrichment [RIP/non-specific (NS)] was calculated by linear conversion of the ΔΔCt. Shown below are the formulas used for the calculation: ΔCt [normalized RIP]=Ct [RIP]−(Ct [Input]−Log 2 (fraction of the input RNA saved))); ΔΔCt [RIP/NS]=ΔCt [normalized RIP]−ΔCt [normalized NS]; Fold Enrichment=2 (−ΔΔCt [RIP/NS]).

Western Blot Analysis:

Brains and spinal cord were homogenized and stored at −80° C. Tissues were homogenized in ice-cold extraction buffer (120 mM NaCl, 50 mM Tris-base (pH 8.0) supplemented with 1× complete protease inhibitor mixture (Roche Applied Science)) straight after sampling and homogenates were centrifuged 30 min at 17,000×g at 4° C. The resulting pellets were re-homogenized and centrifuged again 30 min at 17,000×g at 4° C. Supernatants were resolved on SDS-PAGE followed by immunoblotting with antibodies.

Behavioral Tests

For all of behavioral studies, 15 conditional neuron-specific HuR-deficient mice (Thy1$^{Cre-ERT2-EYFP}$HuR$^{f/f}$, designed as KO) and 15 age matched control mice (Thy1$^{Cre-ERT2-EYFP}$HuR$^{f/+}$, designed as wild type, WT) of both sexes were used (specifically, 8 WT males, 8 KO males, 7 WT females and 7 KO females were used).

Open Field Behavioral Test:

Experimental mice were placed at the periphery of the open field apparatus with the head facing toward the proximal wall and allowed to explore the arena freely for 15 min. The experimenter was out of view from the mice at all times. The distance traveled were automatically recorded on either a video-tracking system or infrared sensors. Measurements were taken over two weeks, twice per week; N=15 for both groups.

Rotarod:

To assess motor coordination and locomotion, the accelerating rotarod (Rotarmex-5, Columbus Instruments, Columbus, Ohio) was utilized. Each mouse received baseline training. Rod rotations increased from 4 to 40 rotations per minute (RPM) during each five-minute trial. An average latency to fall over four trials with a 30 min. inter-trial interval. was calculated for each testing day and compared across all between the two groups. Measurements were taken over two weeks, one time per week; N=15 for both groups.

Y-Maze:

Each mouse was placed in the Y-maze and manually scored for spontaneous alternations (the sequential entry of all arms before entering another arm) and total arm entries. Each mouse was tested at 7, 31, 61, and 91 DPI. At the beginning of each trial, the mouse was placed in the center of the Y-maze and allowed to freely explore for 5 minutes. N=15 for both groups. Measurements were taken over two weeks, twice per week; N=15 for both groups.

Grip Strength:

mice were subject to quantitative grip-strength assessment using a commercial apparatus (BioSeb, Chaville, France). Forelimb and hindlimb grip strength were measured following the manufacturer's instructions. For each experiment, measurements were taken over two weeks, one time per week. N=15 for both groups.

Gene Ontology Term Enrichment Analysis:

GO analysis was performed on the web server of the DAVID functional annotation tool (PMID: 19131956). A FDR of 10% was applied to evaluate significance.

Gene Array:

RNA samples from whole brain tissue of three pairs of experimental neuron-specific HuR-deficient mice and littermate control mice were analyzed on Affymetrix Mouse Gene 2.0 ST arrays. Biotinylated RNA was prepared according to Affymetrix WT Plus Labeling Kit from 150 ng total RNA. The labeled RNA were hybridized for 16 hr at 45° C. on GeneChip 2.0 Arrays. GeneChips were washed and stained in the AffymetrixFluidics Station 450. GeneChips were scanned using the Affymetrix GeneChip Scanner 3000. The full microarray data has been deposited in the NCBI GEO as series GSE112678.

Quantitative Real-Time PCR

Total RNA was isolated with TRIzol reagent (Invitrogen). Real-time PCR was performed using a SYBR Green PCR Master Mix kit (Applied Biosystems). The primers used are presented in Table 1.

Results

Generation of Neuron-Specific HuR-Deficient Mice

To examine the function of the RNA-binding protein HuR in neurons, we generated HuR$^{f/f}$ mice and bred onto Thy1$^{Cre-ERT2-EYFP}$ to obtain conditional neuron-specific HuR-deficient mice (Thy1$^{Cre-ERT2-EYFP}$HuR$^{f/f}$, designed as KO) and control mice (Thy1$^{Cre-ERT2-EYFP}$HuR$^{f/+}$, designed as wild type, WT). Cre expression was induced through Tamoxifen administration to conditional neuron-specific HuR-deficient mice (Thy1$^{Cre-ERT2-EYFP}$HuR$^{f/f}$) and control mice (Thy1$^{Cre-ERT2-EYFP}$HuR$^{f/+}$) of either sex at 10 and 11 weeks of age (FIG. 1 Panel A). Cre-YFP expression was highly induced 21 days after first tamoxifen administration (FIG. 1 Panel B). Notably, western blot analysis revealed that HuR expression was diminished in brain tissue of the conditional neuron-specific HuR-deficient mice (Thy1$^{Cre-ERT2-EYFP}$HuR$^{f/f}$) compared to control mice (Thy1$^{Cre-ERT2-EYFP}$HuR$^{f/+}$) (FIG. 1 Panel C). The residual HuR protein in brain tissue of the conditional neuron-specific HuR-deficient mice is likely from the cells other than neurons in the brain tissue.

Furthermore, primary neurons (but not astrocytes) isolated from brain tissue of the conditional neuron-specific HuR-deficient mice (Thy1$^{Cre-ERT2-EYFP}$HuR$^{f/f}$) showed diminished expression of HuR compared to control mice (Thy1$^{Cre-ERT2-EYFP}$HuR$^{f/+}$) (FIG. 1 Panel D).

Figure 2:
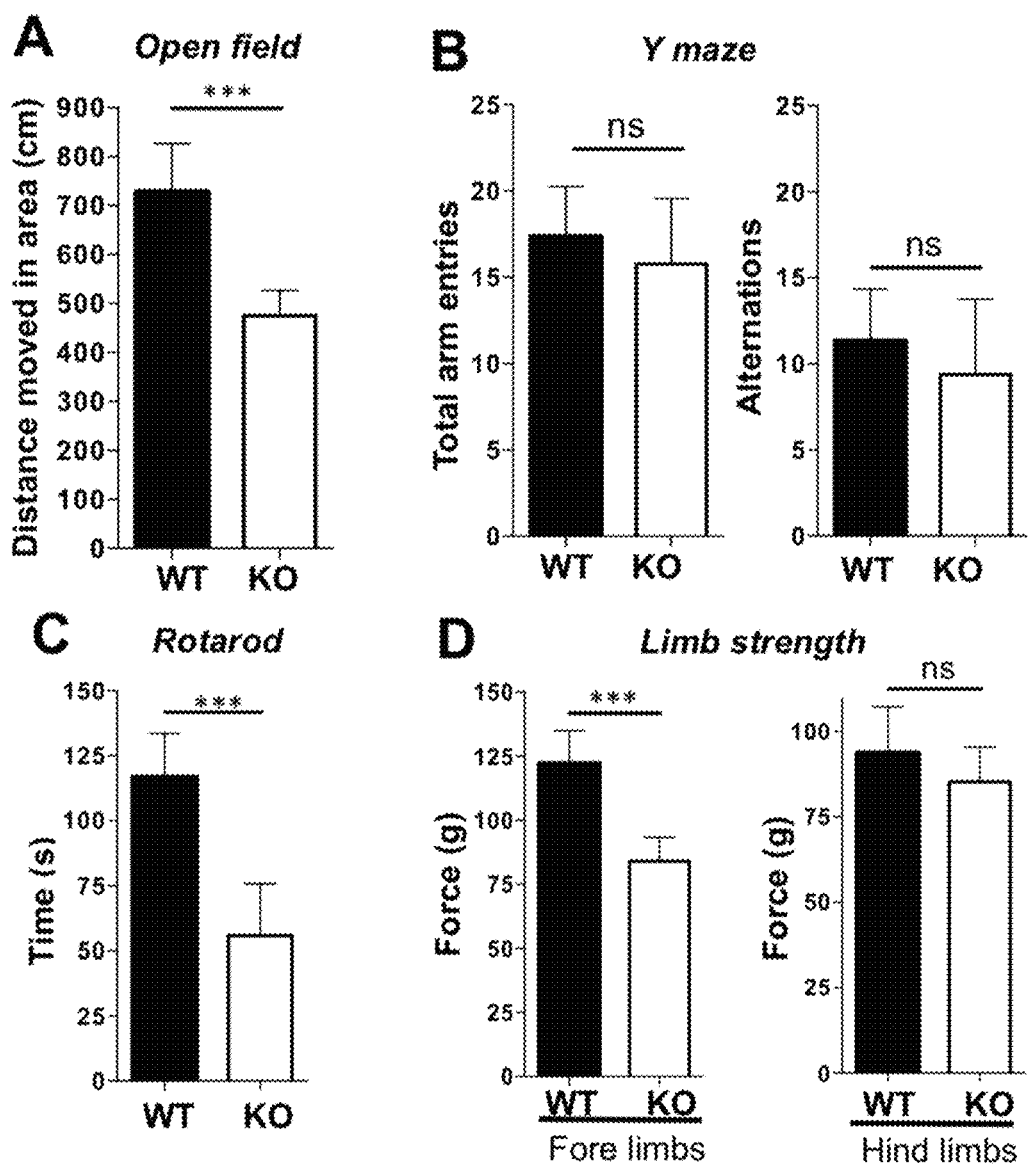
FIG. 2, panels A-D. Neuron-specific HuR-deficient mice show impaired motor coordination and grip strength. Panels A-B. Experimental neuron-specific HuR-deficient and age-matched control mice as described in FIG. 1 Panel A were subjected either to an open field behavioral test for 15 minutes (Panel A) or a Y-maze test for 15 minutes (Panel B). N=15 mice per group. Error bars represent s.d. of biological replicates. *p<0.001 by by two-tailed Student's t test. Panel C. Motor performance of experimental neuron-specific HuR-deficient and control mice as described in FIG. 1 Panel A was compared by a rotarod test with a rod (3 cm in diameter) starting at an initial rotation of 4 rpm and accelerating to 40 rpm over 5 min. Mice were tested for time spent on the rod during each of four trials with a 30 min. inter-trial interval. Each trial was completed when the mouse fell off of the rod. N=15 mice per group. Error bars represent s.d. of biological replicates. *p<0.001 by two-tailed Student's t test. Panel D. Five successful forelimb and hindlimb strength measurements within 2 minutes per mouse were performed. Tests was repeated twice with a 1 week rest period. N=15 mice per group. Error bars represent s.d. of biological replicates. ***p<0.001 by two-tailed Student's t test. Please provide scale bars for the applicable photos in each figure.

Neuron-Specific HuR-Deficient Mice Show Impaired Motor Coordination and Grip Strength Neuron-specific HuR-deficient mice developed a phenotype consisting of poor motor skills and abnormal gait that resembled "wobbler mice" in gross observation, indicating symptoms of motor neuron disease. This phenotype was quantified using a variety of behavioral tests to further confirm the motor deficits. First, we conducted general assessments of basal locomotor activity and evaluated exploration in an open field. Mice were placed in an open area for 15 minutes and overall distance walked was measured. The conditional neuron-specific HuR-deficient mice (Thy1$^{Cre-ERT2-EYFP}$HuR$^{f/+}$) covered significantly less distance (~500 cm) compared to age-matched control (Thy1$^{Cre-ERT2-EYFP}$HuR$^{f/+}$) mice (~700 cm; P<0.05) (FIG. 2vA). In order to determine whether HuR deficiency had any cognitive impact, we also performed a Y-maze test to test exploratory behavior. Mice were placed in a Y-shaped maze and the number of times the mice alternated between arms of the maze was measured and compared to the number of total arm entries. No significant differences in exploratory behavior were found between the conditional neuron-specific HuR-deficient mice (Thy1$^{Cre-ERT2-EYFP}$HuR$^{f/f}$) and control mice (Thy1$^{Cre-ERT2-EYFP}$HuR$^{f/+}$) (FIG. 2 Panel B), indicating that the result from the open field test was probably not caused by cognitive impairment, but rather by impaired motor function.

To further characterize motor function impairments, we employed the rotarod test, which measures coordination, balance, and motor skills. Mice were placed on a rod that rotated with increasing speed and the time they remained on the rod before falling was recorded. During the test, the conditional neuron-specific HuR-deficient mice (Thy1$^{Cre-ERT2-EYFP}$HuR$^{f/f}$), performed significantly worse (~50 seconds) on the rotarod compared to control (Thy1$^{Cre-ERT2-EYFP}$HuR$^{f/+}$) mice (~120 seconds; P<0.05), indicating coordination deficiency (FIG. 2 Panel C). In order to assess muscle strength as an indicator of neuromuscular function, we tested grip strength of the forelimbs and hindlimbs by pulling them against a metal mesh and measuring the force by which they held on. It was found that the forelimbs grip strength of the conditional neuron-specific HuR-deficient mice (Thy1$^{Cre-ERT2-EYFP}$HuR$^{f/f}$) was (~120 g), which was much weaker than that of the control (Thy1$^{Cre-ERT2-EYFP}$HuR$^{f/+}$) mice (~85 g), although hindlimb strength did not show any significant differences (FIG. 2 Panel D).

It is important to point out that we also analyzed the data based on gender and no significant difference in behavior was observed between male and female mice (data not shown). The differences between conditional neuron-specific HuR-deficient mice (Thy1$^{Cre-ERT2-EYFP}$HuR$^{f/f}$) and control mice in the behavioral tests (FIGS. 2A, 2C and 2D) stand with gender controlled.

Figure 3:
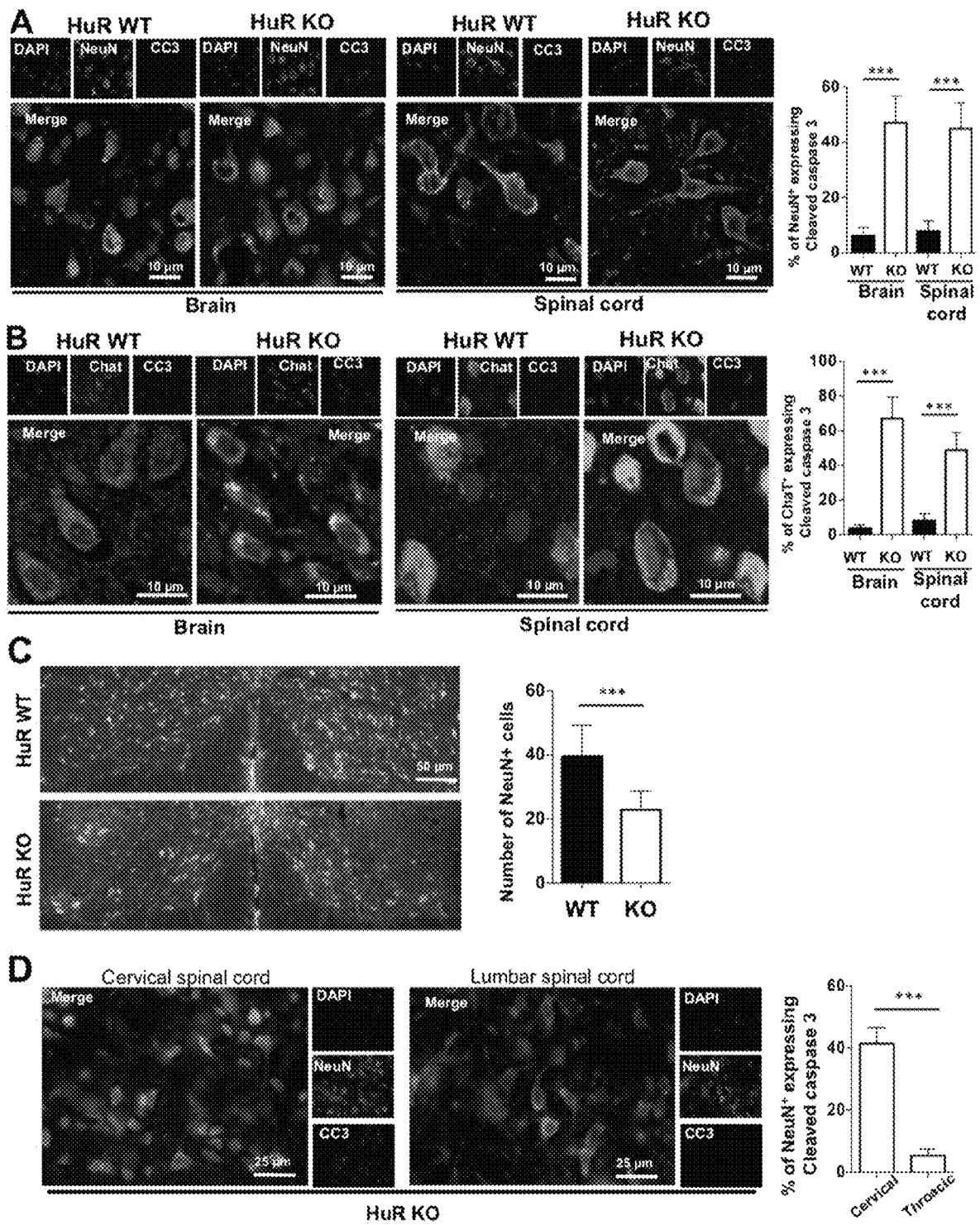
FIG. 3, panels A-D. Neuron-specific HuR-deficient mice display degeneration of cortical and spinal motor neurons. Panels A-B. The representative confocal images of either NeuN (green) and cleaved caspase 3 (red) double staining (Panel A) or ChaT (green) and cleaved caspase 3 (red) double staining (Panel B) in sections of primary motor cortex in brain and ventral horn of cervical spinal cord of experimental neuron-specific HuR-deficient and control mice as described in FIG. 1 Panel A. Nuclei were stained with DAPI (blue). The percentages of neurons that were caspase 3-positive over NeuN-positive were quantified for brain and spinal cord sections, respectively. N=15 mice per group and 5 sections per mouse were analyzed. Error bars represent s.d. of biological replicates. *p<0.001 by Mann-Whitney test. Panel C. The representative fluorescent images of NeuN staining indicated the significant reduction of NeuN positive cells (~40%) in cervical spinal cord (Layers VIII and IX) of experimental neuron-specific HuR-deficient than control mice. The number of neurons in the ventral horn of the spinal cord was quantified by counting NeuN-positive cells. N=15 mice per group and 5 sections per mouse were analyzed. Error bars represent s.d. of biological replicates. *p<0.001 by Mann-Whitney test. Verg D. The representative fluorescent images of NeuN (green) and cleaved caspase 3 (red) double staining in cervical and lumbar spinal cord of experimental neuron-specific HuR-deficient and control mice as described in FIG. 1A. Nuclei were stained with DAPI (blue). N=15 mice per group and 5 sections per mouse were analyzed. Error bars represent s.d. of biological replicates. ***p<0.001 by Mann-Whitney test.

Neuron-Specific HuR-Deficient Mice Display Degeneration of Cortical and Spinal Motor Neurons We then examined whether there was any neuronal pathology that might account for the impaired motor coordination and grip strength in neuron-specific HuR-deficient mice. We performed immunostaining of brain sections from neuron-specific HuR-deficient mice and littermate controls using anti-NeuN (neuron-specific marker), anti-ChaT (motor neuron marker) and anti-cleaved Caspase 3 (apoptotic cells marker). We found that there was an increased number of apoptotic neuronal cells (~8-fold greater cleaved caspase 3-positive cells) in neuron-specific HuR-deficient mice compared to wild-type mice (FIG. 3 Panel A). Levels of cleaved Caspase 3 were especially high in pyramidal neurons, which correlated with the high levels of Cre expression in these cells (FIG. 1 Panel B). Furthermore, we found a ~7-fold increase in cleaved Caspase 3-positive cells in the cervical spinal cord of neuron-specific HuR-deficient mice compared to wild-type controls, indicating significant progress of neuronal cell death in the HuR-deficient cervical spinal cord (FIG. 3 Panel B). Additionally, the total number of neurons in the ventral horn (layers VIII and IX), was quantified in both groups. We identified significant neuronal loss in these layers in HuR-deficient mice, including large motor neurons (FIG. 3C). However, immunostaining of the lumbar spinal cord of neuron-specific HuR-deficient mice showed little cleaved Caspase-3 compared to that in the cervical spinal cord, indicating significantly less cell death in the lumbar spinal cord of neuron-specific HuR-deficient mice (FIG. 3D). These findings are consistent with the results of the grip strength test, in which the forelimbs were significantly weakened but the hindlimbs were not.

Microarray Analysis of Brain Tissue from Neuron-Specific HuR-Deficient Mice

Figure 4:
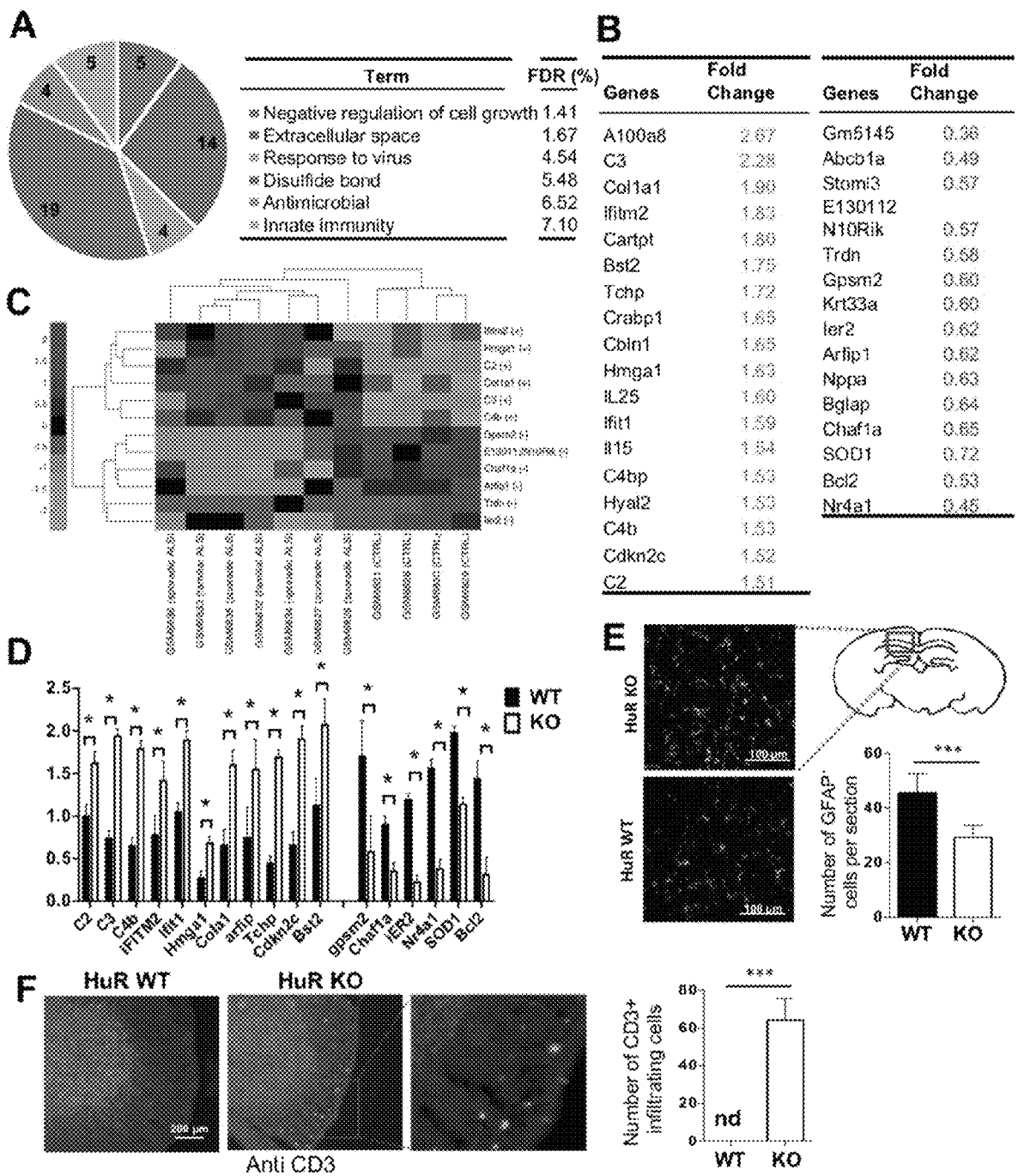
FIG. 4, panels A-F. Microarray analysis of brain tissue from neuron-specific HuR-deficient mice. A. RNA samples from whole brain tissue of three pairs of experimental neuron-specific HuR-deficient mice and littermate control mice were analyzed on Affymetrix Mouse Gene 2.0 ST arrays. Differentially up- and down-regulated genes (>1.5-fold) were subjected to Ontology (GO) enrichment analysis. The significantly enriched (False Discovery Rate (FDR) <10%) GO terms and the numbers of pathway-associated genes are shown. Panel B. Lists of selected differentially expressed transcripts identified by microarray analysis as described in FIG. 4 Panel A. Panel C. Heatmap showing the level of expression of the selected transcripts in ALS patients and controls, which were differentially expressed between neuron-specific HuR-deficient and control mice. The plus (+) and minus (−) signs represent up- and down-regulation of transcripts, respectively. The expression profile was standardized along the row for better visualization. The red and green colors indicate high and low expression, respectively. Panel D. Real-time PCR analysis of the selected transcripts (identified in microarray analysis) was performed for RNA samples from brain tissue of experimental neuron-specific HuR-deficient mice and littermate control mice. N15 mice per group. Error bars represent s.d. of biological replicates. *P<0.001 by by two-tailed Student's t test. Panel E. The representative confocal images of GFAP (green) staining in brain sections of experimental neuron-specific HuR-deficient and control mice as described in FIG. 1 Panel A. Nuclei were stained with DAPI (blue). Bar graph shows the number of GFAP-positive cells per section. N-15 mice per group and 5 sections per mouse were analyzed. Error bars represent s.d. of biological replicates. *p<0.001 by Mann-Whitney test. Panel F. Anti-CD3 stained thoracic spinal cord sections of experimental neuron-specific HuR-deficient and control mice as described in FIG. 1 Panel A. N15 mice per group and 5 sections per mouse were analyzed. Error bars represent s.d. of biological replicates. ***p<0.001 by Mann-Whitney test.

To investigate the possible mechanism for how neuron-specific HuR deficiency impacts neuropathology, we then performed genome-wide microarray analysis using brain tissues from neuron-specific HuR-deficient and control mice. We identified a total of 3516 genes that showed significant differential expression in the brain tissues of neuron-specific HuR-deficient mice compared to control mice. Gene Ontology (GO) enrichment analysis of the significantly altered genes showed that the most significantly enriched GO term for HuR-regulated transcripts was 'negative regulation of cell growth' (FIG. 4 Panel A). Consistent with the neuronal cell death observed in the brain and spinal cord of neuron-specific HuR-deficient mice, the transcripts listed under this GO term were significantly up-regulated in brain tissue of neuron-specific HuR-deficient mice compared to littermate controls and included trichoplein keratin filament-binding protein (Tchp, which is a tumor suppressor protein) and Cdkn2c (which prevents the activation of CDK kinases and functions as a cell growth regulator that controls cell cycle G1 progression) (FIG. 4 Panels A-B; 4 Panel D). Interestingly, the additional enriched GO terms were largely related to inflammation. It is intriguing that many of the inflammatory genes were actually up-regulated, including interferon-induced genes (e.g. iFI™2, Ifit1, and Bst2) and complement genes (e.g. C2, C3, and C4b) (FIG. 4 Panels A-B; 4 Panel D).

Neuron-Specific HuR-Deficient Mice Display a Molecular Signature Reminiscent of ALS Considering the impaired function in motor neurons, we compared the list of genes that were differentially expressed in the brain tissues of neuron-specific HuR-deficient mice with the GEO database for ALS patients. We identified a group of genes from our array analysis that were also significantly altered in the brain and spinal cord of ALS patients (FIG. 4 Panel C). Among the downregulated genes (FIG. 4 Panels B-D), we identified additional genes involved in cell differentiation and proliferation, including G-Protein Signaling Modulator 2 (GPSM2, which has been shown to play a role in neuroblast division and mitotic spindle pole organization) and Immediate Early Response 2 (IER2, which is a transcription factor involved in regulating neuronal differentiation). These findings suggest that HuR might play a role in stabilizing the transcripts of genes crucial for cell differentiation and division, which helps to explain the increased neuronal cell death observed in HuR-deficient mice. Furthermore, some of the upregulated genes shared by neuron-specific HuR-deficient mice and ALS patients were inflammatory genes (FIG. 4 Panels B-D), including complement components (C2, C3, and C4b) and interferon-induced genes (including iFitm2, Ifit1). Astrogliosis has been implicated in ALS. Using intermediate filament, glial fibrillary acid protein (GFAP) as a marker, we indeed observed increased astrocyte activation/expansion in the brain section of the neuron-specific HuR-deficient mice compared to that of control mice (FIG. 4 Panel E). These results suggest that the astrogliosis may contribute to the observed inflammation in the brain tissue of the Neuron-specific HuR-deficient mice. Additionally, we detected increased T cell infiltration in the spinal cord of neuron-specific HuR-deficient mice compared to wild-type control mice (FIG. 4 Panel F).

One question is whether there is a direct HuR target(s) among the HuR-regulated transcripts that we identified using neuron-specific HuR-deficient mice and the GEO database for ALS patients (11). Ier2 was found to be an mRNA target of HuR (12). To assess RNA binding of HuR to Ier2 mRNA in neuronal cells, we immunoprecipitated HuR from NSC-34 motor neuron-like cells, followed by RT-PCR analysis. Enriched Ier2 mRNA was detected in HuR immunoprecipitates compared to those from IgG immunoprecipitation controls (FIG. 5A), suggesting direct HuR binding to Ier2 mRNA in neuronal cells. In support of this, RT-PCR and western blot analysis showed reduced expression of Ier2 in brain tissue of neuron-specific HuR-deficient mice (FIG. 4 Panel D and 5 Panel B).

Figure 5:
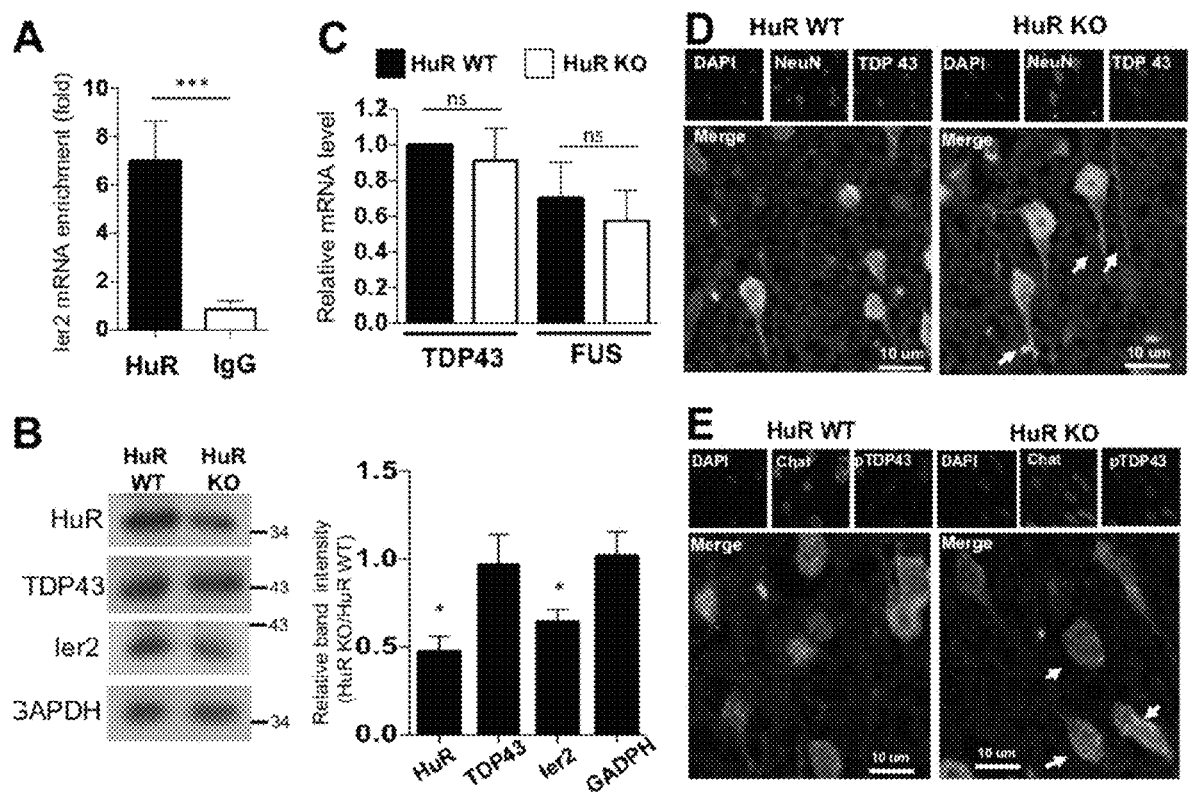
FIG. 5, panels A-E. Neuron-specific HuR-deficient mice display a molecular signature consistent with ALS. Panel A. Lysates of NSC-34 cells were subjected to RNA immunoprecipitation with anti-HuR or anti-IgG antibody, followed by RT-PCR analysis of Ier2 mRNA. Error bars represent s.d. of biological replicates (N=15 mice for both KO and WT). *p<0.001, by two-tailed unpaired Student's t test. Panel B. Whole brain extracts from experimental neuron-specific HuR-deficient and control mice as described in FIG. 1 Panel A were analyzed by Western blotting with the indicated antibodies. Western blots were quantified by densitometry using ImageJ, error bars represent s.d. of biological replicates (N=15 mice for both KO and WT), *P<0.001 by two-tailed Student's t test. C. Real-time PCR analysis of TDP-43 and FUS mRNA in RNA samples from whole brain tissue of experimental neuron-specific HuR-deficient and control mice. Error bars represent s.d. of biological replicates (N=15 mice for both KO and WT). ***p<0.001, by two-tailed unpaired Student's t test. Panels D-E. The representative confocal images of either NeuN (green) and TDP-43 (red) (D) or ChaT (green) and phospho-TDP-43 (red) (Panel E) double staining in brain sections of experimental neuron-specific HuR-deficient and control mice. Nuclei were stained with DAPI (blue).
Figure 6:
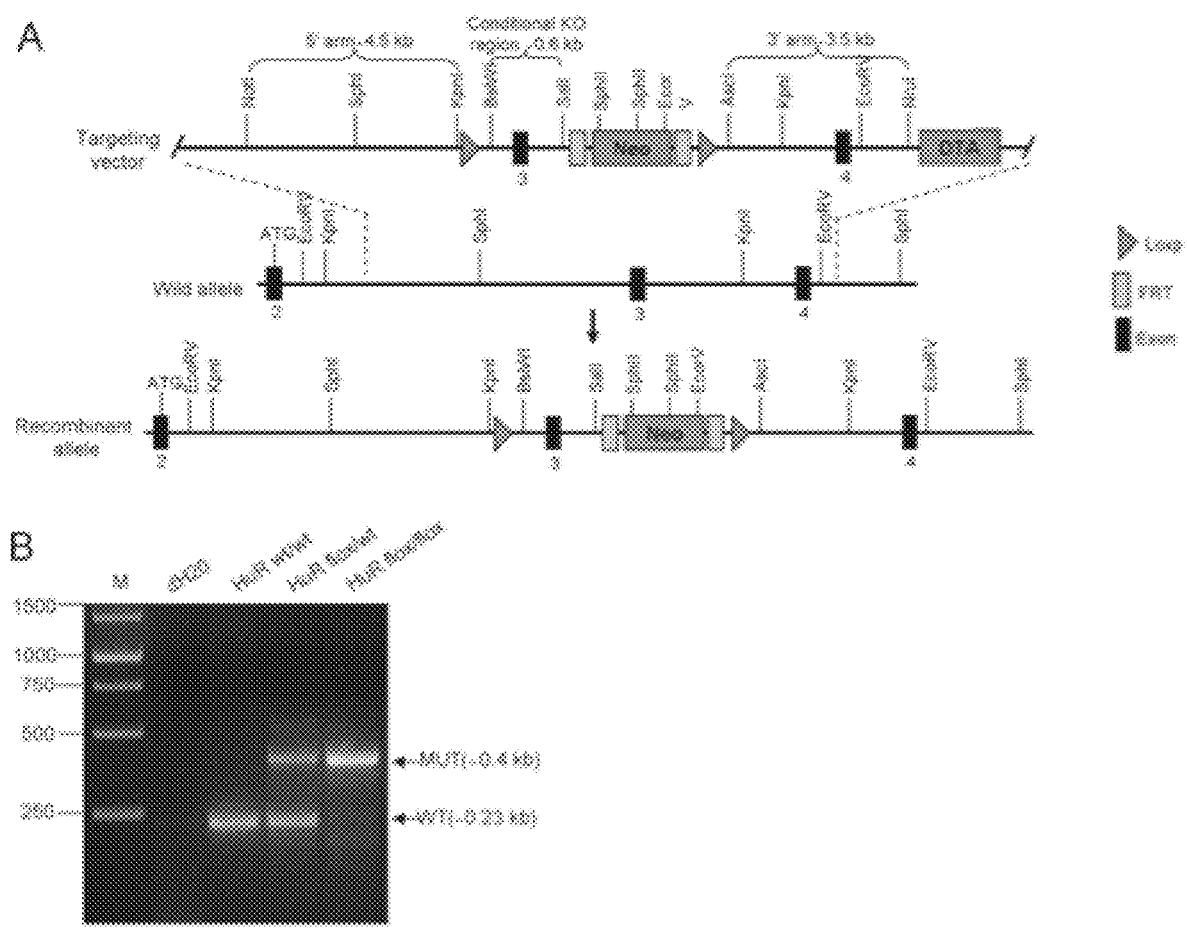
FIG. 6, panels A-B—Conditional HuR-knockout (KO) embryonic stem (ES) cells and mice were generated using gene-targeting technology. A targeting vector containing a 59homology arm (4.5 kb), a 39homology arm (3.5 kb), and a conditional region (0.6 kb) was generated by PCR. The targeting construct also contained loxP sequences flanking the conditional KO region, the Neo expression cassette (for positive selection of ES cells) flanked by FRT sequences (for subsequent removal of the Neo cassette), and a DTA expression cassette (for negative selection of the potentially targeted ES cells). The final targeting construct is shown in FIG. 6A. Successfully targeted ES cells were injected into blastocysts and implanted into pseudopregnant females. Chimeric male offspring were mated to WT C57BL/6 female, and germline transmission of the mutant HuR allele was confirmed by Southern blot (data not shown) and PCR analyses (FIG. 6B). The following primers were used: Neo expression cassette forward: 59-GGTTTC-CAAATGTGTCAGTTTCATAGC-39 (SEQ ID NO:1), intron 3 re-verse: 59-AGAGATAGATGGTTAGGCAT-AGAGATGCAG-39 (SEQ ID NO:2), and intron 3 forward: 59-TATGCTTTAAGAGACCCAGAAGCCAG-39 (SEQ ID NO:3).

Since HuR was implicated in positively regulating TDP-43 and FUS expression in astrocytes, we examined the impact of neuron-specific HuR deficiency on TDP-43 and FUS expression. We failed to detect significant impact of neuron-specific HuR deficiency on TDP-43 or FUS expression in brain tissue by both RT-PCR and western blot analysis (FIG. 5 Panels B-C). However, neuronal HuR deficiency did result in the redistribution of TDP-43 to cytosolic granules (FIG. 5 Panel D), which has been linked to motor neuron disease (13, 14).

We have created a neuron-specific HuR-deficient mouse strain to study a HuR function/phenotype that can be used as a motor neuron disease model. Second, neuron-specific HuR-deficient mice show significant deficits in forelimb motor function that are supported by anatomical evidence of motor neuron death in both motor cortex and cervical spinal cord. Third, microarray analysis revealed reductions in several hallmark molecules of ALS in neuron-specific HuR-deficient mice, as well as significant up-regulation of inflammation-related genes similar to those found in ALS patients.

The present Example showed significant motor neuron death in HuR-deficient mice. The loss of HuR in neurons not only alters gene expression, but also increases sensitivity to neurotoxicity and oxidative stress (18). Both post-mortem tissues from ALS patients and transgenic mice expressing mutant SOD1 have revealed a role of oxidative stress in the pathogenesis of ALS (19-21). A recent report indicated a possible link between oxidative stress and TDP-43 delocalization (from nucleus to cytoplasm) and aggregation in the cytosol (13, 22). In the present Example, we have demonstrated delocalization of TDP-43 from nuclei to cytosol in cortical neurons from HuR-deficient mice, suggesting that increased oxidative stress leads to neuronal death in this model.

In addition to neuropathology, neuron-specific HuR-deficient mice also displayed a molecular signature consistent with motor neuron disease. We identified a group of genes from our array analysis that were also significantly altered in the brain and spinal cord of ALS patients. Genome-wide microarray analysis and RT-PCR analysis indicated that HuR deficiency in neurons reduced the expression of genes important for cell survival and proliferation, including SOD1, Ier2, and GPSM2. Excitingly, while SOD1 mutation is well-known to be associated with ALS, the expression of Ier2 and GPSM2 were also significantly reduced in the brain and spinal cord of ALS patients (11). Notably, out of the 3500 genes differentially expressed in the brain tissues of neuron-specific HuR-deficient mice, the most significantly enriched GO term for HuR-regulated transcripts was regulation of cell growth, which is an important molecular signature of motor neuron diseases.

Interestingly, the additional enriched GO terms for HuR-regulated transcripts were largely related to inflammation, including complement components and interferon-induced genes. Interestingly, we found that there was increased astrocyte activation in the brain tissue of neuro-specific HuR-deficient mice. Inflammation and astrogliosis have been associated with several neurodegenerative disorders and detected in the brainstem and spinal cord of patients with ALS and in mouse models of this disease (23-25). The complement system has been implicated in ALS pathogenesis; specifically, in an ALS mouse model in which SOD1 was mutated (G93A), deposition of C1q and C3/C3b was found along peripheral nerves, in the spinal cord, and in brain tissue (26-31). Recent findings indicate that, under stress, local complement signaling might therefore promote damage and motor neuron death in ALS (31). However, the exact role of the complement system in ALS pathogenesis and progression remains unclear. Another immune gene found upregulated in ALS patients and in HuR-deficient brain tissue was Interferon Induced Transmembrane Protein 2 (Ifitm2), which has been found to mediate apoptosis by caspase activation, potentially contributing to neuronal cell death in the HuR-deficient mice as indicated by Caspase 3 cleavage. Of note, reduction or deletion of IFNα receptor 1 inhibited IFN signaling and increased the life-span of SOD1 (G93A) mice (32). It is possible that neuronal cell death releases a danger signal, which in turn activates immune cells to produce interferons, resulting in the induction of interferon-responsive genes. Additionally, we observed increased immune cell infiltration in the spinal cord of neuron-specific HuR-deficient mice. While astrogliosis has been implicated in the recruitment of leukocytes to the sites of axonal injury in the CNS, T cells have also been shown to be associated with neuroprotective role in ALS possibly by modulating a beneficial inflammatory response to neuronal injury (33). Future studies are required to further analyze the T cell subsets and their functions in the brain tissues of neuro-specific HuR-deficient mice.

We also searched for the direct HuR target(s) among the many regulated targets altered in HuR-deficient brain and in the CNS of ALS patients. Although HuR was implicated in positively regulating TDP-43 and FUS expression in astrocytes, we failed to detect any significant impact of neuron-specific HuR deficiency on TDP-43 or FUS expression in brain tissue. Instead, we found that Ier2 might be an mRNA target of HuR (12). RT-PCR, western blot analysis, and immunostaining demonstrated reduced expression of Ier2 in brain tissue of neuron-specific HuR-deficient mice. Moreover, enriched Ier2 mRNA was detected in HuR immunoprecipitates compared to those from IgG controls, suggesting HuR-direct binding to Ier2 mRNA in neuronal cells. Importantly, Ier2 mRNA was also significantly reduced in the brain and spinal cord of ALS patients (11). Although TDP-43 was not a direct target of HuR in neuronal cells, neuronal HuR deficiency did result in the redistribution of TDP-43 to cytosolic granules, which has been linked to motor neuron disease. Neuron-specific HuR-deficient mice have a motor neuron deficiency phenotype accompanied by both neuropathology and molecular signatures manifested in ALS patients.

REFERENCES

1. Taylor, et al., Cleveland. 2016. Decoding ALS: from genes to mechanism. *Nature* 539: 197-206.
2. Zarei et ak., 2015. A comprehensive review of amyotrophic lateral sclerosis. *Surg. Neurol. Int.* 6.
3. Petrov, et a., 2017. ALS Clinical Trials Review: 20 Years of Failure. Are We Any Closer to Registering a New Treatment? *Front. Aging Neurosci.* 9.
4. Xu, Z.-S. 2012. Does a loss of TDP-43 function cause neurodegeneration? *Mol. Neurodegener.* 7: 27.
5. Brennan, C. M., and J. A. Steitz. 2001. HuR and mRNA stability. *Cell. Mol. Life Sci. CMLS* 58: 266-277.
6. Schoenberg, D. R., and L. E. Maquat. 2012. Regulation of cytoplasmic mRNA decay. *Nat. Rev. Genet.* 13: 246-259.
7. Herjan, et al., 2013. HuR is required for IL-17-induced Actl-mediated CXCL1 and CXCLS mRNA stabilization. *J. Immunol. Baltim. Md.* 1950 191: 640-649.
8. Lu et al., 2014. Hu antigen R (HuR) is a positive regulator of the RNA-binding proteins TDP-43 and FUS/TLS: implications for amyotrophic lateral sclerosis. *J. Biol. Chem.* 289: 31792-31804.
9. Lu, et al., 2009. Amyotrophic lateral sclerosis-linked mutant SOD1 sequesters Hu antigen R (HuR) and TIA-1-related protein (TIAR): implications for impaired post-transcriptional regulation of vascular endothelial growth factor. *J. Biol. Chem.* 284: 33989-33998.
10. Milani, et al., 2013. Posttranscriptional regulation of SOD1 gene expression under oxidative stress: Potential role of ELAV proteins in sporadic ALS. *Neurobiol. Dis.* 60: 51-60.
11. Dangond, et al., 2004. Molecular signature of late-stage human ALS revealed by expression profiling of postmortem spinal cord gray matter. *Physiol. Genomics* 16: 229-239.
12. Abdelmohsen et al., 2009. Ubiquitin-mediated proteolysis of HuR by heat shock. *EMBO J.* 28: 1271-1282.
13. Cohen et al., An acetylation switch controls TDP-43 function and aggregation propensity. *Nat. Commun.* 6: 5845.
14. Dewey, et al., 2012. TDP-43 aggregation in neurodegeneration: are stress granules the key? *Brain Res.* 1462: 16-25.
15. Magrané, et al., 2014. Abnormal mitochondrial transport and morphology are common pathological denominators in SOD1 and TDP43 ALS mouse models. *Hum. Mol. Genet.* 23: 1413-1424.
16. Peters et al., 2015. Emerging mechanisms of molecular pathology in ALS. *J. Clin. Invest.* 125: 1767-1779.
17. Rowland et al., 2001. Amyotrophic lateral sclerosis. *N. Engl. J. Med.* 344: 1688-1700.
18. Skliris et al., 2015. Neuroprotection requires the functions of the RNA-binding protein HuR. *Cell Death Differ.* 22: 703-718.
19. D'Amico et al., 2013. Clinical perspective on oxidative stress in sporadic amyotrophic lateral sclerosis. *Free Radic. Biol. Med.* 65: 509-527.
20. Nagase et al., 2016. Increased oxidative stress in patients with amyotrophic lateral sclerosis and the effect of edaravone administration. *Redox Rep. Commun. Free Radic. Res.* 21: 104-112.
21. Pollari et al., 2014. The role of oxidative stress in degeneration of the neuromuscular junction in amyotrophic lateral sclerosis. *Front. Cell. Neurosci.* 8.
22. Meyerowitz et al., 2011. C-Jun N-terminal kinase controls TDP-43 accumulation in stress granules induced by oxidative stress. *Mol. Neurodegener.* 6: 57.
23. Amor et al., 2010. Inflammation in neurodegenerative diseases. *Immunology* 129: 154-169.
24. McCombe et al., 2011. The Role of Immune and Inflammatory Mechanisms in ALS. *Curr. Mol. Med.* 11: 246-254.
25. Philips and Rothstein. 2014. Glial cells in Amyotrophic Lateral Sclerosis. *Exp. Neurol.* 262PB: 111-120.
26. Heurich, et al., 2011. Complement upregulation and activation on motor neurons and neuromuscular junction in the SOD1 G93A mouse model of familial amyotrophic lateral sclerosis. *J. Neuroimmunol.* 235: 104-109.
27. Humayun et al., 2009. The complement factor C5a receptor is upregulated in NFL−/− mouse motor neurons. *J. Neuroimmunol.* 210: 52-62.
28. Lee, et al., 2013. Dysregulation of the complement cascade in the hSOD1G93Atransgenic mouse model of amyotrophic lateral sclerosis. *J. Neuroinflammation* 10: 119.
29. Lobsiger et al., Cleveland. 2007. Toxicity from different SOD1 mutants dysregulates the complement system and the neuronal regenerative response in ALS motor neurons. *Proc. Natl. Acad. Sci. U.S.A* 104: 7319-7326.
30. Takeuchi et al., 2010. Induction of protective immunity by vaccination with wild-type apo superoxide dismutase 1 in mutant SOD1 transgenic mice. *J. Neuropathol. Exp. Neurol.* 69: 1044-1056.
31. Woodruff, et al., 2008. The complement factor C5a contributes to pathology in a rat model of amyotrophic lateral sclerosis. *J. Immunol. Baltim. Md.* 1950 181: 8727-8734.
32. Julien, et al., 2006. Transgenic mouse models of amyotrophic lateral sclerosis. *Biochim. Biophys. Acta BBA—Mol. Basis Dis.* 1762: 1013-1024.
33. Chiu, et al., 2008. T lymphocytes potentiate endogenous neuroprotective inflammation in a mouse model of ALS. *Proc. Natl. Acad. Sci. U.S.A* 105: 17913-17918.

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

We claim:

1. A transgenic mouse whose genome comprises:
   i) a floxed endogenous HuR gene; and
   ii) a nucleic acid sequence encoding recombinase operably linked to a neuron-specific promoter, wherein the endogenous HuR gene is specifically inactivated in neurons of said mouse, and said mouse has:
   a) impaired motor coordination;
   b) impaired grip strength;
   c) degeneration of cortical motor neurons; and
   d) degeneration of spinal motor neurons.

2. The transgenic mouse of claim 1, wherein the genome of said mouse is heterozygous for the floxed endogenous HuR gene.

3. A method of screening test compounds, the method comprising:
   A) administering an inducing agent to a transgenic mouse such that an endogenous HuR gene is inactivated specifically in neurons, wherein said transgenic mouse has:
      i) a genome comprising:
         a) a floxed endogenous HuR gene; and
         b) a nucleic acid sequence encoding recombinase operably linked to a neuron-specific promoter; and
      ii) a) impaired motor coordination;
         b) impaired grip strength;
         c) degeneration of cortical motor neurons;
         d) degeneration of spinal motor neurons;
   B) administering a test compound to the transgenic mouse obtained in step A); and
   C) determining whether the test compound treated the impaired motor coordination, impaired grip strength, degeneration of cortical motor neurons, or degeneration of spinal motor neurons in the mouse.

4. The method of claim 3, wherein the test agent is a small molecule.

5. The method of claim 3, wherein the inducing agent is Tamoxifen.

6. The method of claim 3, wherein the neuron-specific promoter is a Thy1 promoter.

7. The method of claim 3, wherein the test compound is a candidate for treating amyotrophic lateral sclerosis (ALS).

* * * * *